United States Patent
Sirén (10) Patent No.: US 10,463,695 B2
(45) Date of Patent: Nov. 5, 2019

(54) METHODS AND COMPOSITIONS FOR USE IN THE PREVENTION, TREATMENT AND/OR ALLEVIATION OF CANCER

(71) Applicant: Matti J. Sirén, Helsinki (FI)

(72) Inventor: Matti J. Sirén, Helsinki (FI)

(*) Notice: Subject to any disclaimer, the term of this patent is extended or adjusted under 35 U.S.C. 154(b) by 368 days.

(21) Appl. No.: 15/409,754

(22) Filed: Jan. 19, 2017

(65) Prior Publication Data

US 2017/0202881 A1 Jul. 20, 2017

(30) Foreign Application Priority Data

Jan. 19, 2016 (SE) .................................... 1650058

(51) Int. Cl.
*A61K 35/14* (2015.01)
*A61K 33/30* (2006.01)
*A61K 35/16* (2015.01)
*A61K 45/06* (2006.01)
*C12N 5/00* (2006.01)

(52) U.S. Cl.
CPC .............. *A61K 35/14* (2013.01); *A61K 33/30* (2013.01); *A61K 35/16* (2013.01); *A61K 45/06* (2013.01); *C12N 5/0018* (2013.01); *C12N 2500/10* (2013.01); *C12N 2500/22* (2013.01)

(58) Field of Classification Search
None
See application file for complete search history.

(56) References Cited

U.S. PATENT DOCUMENTS

2013/0337440 A1 12/2013 Antes

OTHER PUBLICATIONS

Gunn et al. "Cadmium-Induced Intentltial Cell Tumors in Rats and Mice and Their Prevention by Zinc" J Natl Cancer Inst. Oct. 1963; 31:745-59.*
Mayo Clinic "Tests and Procedures: Cancer Treatment" 3 pgs published Jun. 27, 2013.*
McCarty et al. "Zinc and multi-mineral supplementation should mitigate the pathogenic impact of cadmium exposure" Medical Hypotheses 79 (2012) 642-648.*
Ogunlewe et al. "Zinc and Cadmium Concentrations in Indigenous Blacks With Normal, Hypertrophic, and Malignant Prostate" Cancer Apr. 1, 1989, 1388-1392 (Year: 1989).*
International Search Report for corresponding International Application No. PCT/EP2017/051091, dated Apr. 13, 2017, 7 pgs.
J. McClung et al., "The influence of zinc status on the kinetics of zinc uptake into cultured endothelial cells", The Journal of Nutritional Biochemistry, vol. 10, No. 8, Aug. 1, 1999, pp. 484-489.
H. Haase et al., "The biochemical effects of extracellular Zn2+ and other metal ions are severely affected by their speciation in cell culture media", Metallomics, vol. 7, No. 1, Jan. 1, 2015, pp. 102-111.
Christopher M. R. Bax et al., "Human Fetal Endothelial Cells Acquire Zinc (11) from Both the Protein Bound and Nonprotein Bound Pools in Serum Bax and Bloxam Introduction", Biological Trace Element Research, Mar. 15, 1997.
M. Webb et al., "Platcental transport and embryonic utilization of essential metabolites in the rat at the teratogenic dose of cadmium", Journal of Applied Toxicology, vol. 1, No. 5, Oct. 1, 1981, pp. 270-277.
Ana Lucia Vargas Arigony et al., "The Influence of Micronutrients in Cell Culture: A Reflection on Viability and Genomic Stability", Biomed Research International, vol. 2013, Jan. 1, 2013, pp. 1-22.

* cited by examiner

*Primary Examiner* — Thane Underdahl
(74) *Attorney, Agent, or Firm* — Tucker Ellis LLP (57) ABSTRACT

The ratio of zinc and cadmium is of significance for error-free proliferation and differentiation of cells. An understanding of the role of cadmium in the etiology of cancer offers possibilities to gain a better understanding of cancer as well as possibilities to prevent, treat and/or alleviate cancer. The concentration of Zn(II) in fetal serum, human serum from umbilical cord blood or healthy donors, and in avian serum including intact eggs and egg products has significance for the reliability and repeatability of cell and tissue culture method using said serum, or serum containing products, or eggs. Disclosed is a method in the manufacture of serum products, in particular serum products intended for use in in vitro culture of mammalian cells or tissues, wherein the concentration of Zn(II) is determined, and preferably adjusted to a desired interval. Different products consisting of or containing serum or serum fractions are also disclosed.

15 Claims, 2 Drawing Sheets

METHODS AND COMPOSITIONS FOR USE IN THE PREVENTION, TREATMENT AND/OR ALLEVIATION OF CANCER

RELATED APPLICATION DATA

This application claims the benefit of Swedish Application No. 1650058-9 filed Jan. 19, 2016, the disclosure of which is incorporated herein by reference in its entirety.

TECHNICAL FIELD

The present disclosure investigates the etiology of cancer, and proposes new principles of preventing, treating or alleviating cancer in mammalian subjects.

The present disclosure also relates generally to improvements in the production and use of blood products, serum products, and cell growth media, in particular to such products consisting or comprising fetal serum of different origin, but not limited thereto. Avian serum and egg products are also relevant growth media, which can be subjected to modifications based on the findings and methods disclosed herein.

Blood products intended for administration to human patients, such as whole blood products, serum and plasma products, and blood fractions, are also comprised herein.

BACKGROUND

Cancer is a collective term for diseases caused by an uncontrolled division of cells in the body. Frequently the term refers specifically to the malignant growth or tumor resulting from such uncontrolled division of cells. Historical records show that cancer has scared and eluded humanity since ancient times. In the world of today, with better healthcare and increasing lifespans, the prevalence of cancer seems to have increased. While some forms of cancer can be cured, the outcome is far from certain, and cancer still remains an enigmatic and frightening diagnosis.

In his award winning book "The Emperor of All Maladies: A Biography of Cancer", Siddhartha Mukherjee, Ph.D., M.D. states that "it is unclear whether an intervention that discriminates between malignant and normal growth is even possible. Perhaps cancer, the scrappy, fecund, invasive, adaptable twin to our own scrappy, fecund, invasive, adaptable cells and genes, is impossible to disconnect from our bodies. Perhaps cancer defines the inherent outer limit of our survival. As our cells divide and our bodies age, and as mutations accumulate inexorably upon mutations, cancer might well be the final terminus in our development as organism."

The present inventor however disagrees with the above conclusion. Instead, the present inventor notes that there is a phase in the development of mammals when cell proliferation is extremely fast and efficient, but during which there are very few if any occurrences of cancer. This is the gestation period, i.e. the time in which a fetus develops, beginning with fertilization and ending with birth. The duration of this period varies between species. In humans, the gestation period is about nine months. Smaller, short lived mammals generally have a shorter gestation period, e.g. about 19 to 21 days for mice, and about 31 days for rabbits. Conversely, larger, long lived mammals tend to have a longer gestation period, e.g. about 21 months for elephants, and about 14 to 16 months for sperm whales.

During the gestation period, an extremely rapid cell differentiation and proliferation takes place. It appears that also others have noticed this, for example Vincent T. DeVita Jr. and Elizabeth DeVita-Raeburn in their book "The Death of Cancer: After Fifty Years on the Front Lines of Medicine, a Pioneering Oncologist Reveals Why the War on Cancer is Winnable—and How we can Get There" (Sarah Crichton Books, 2015) conclude that "embryonic cells have only nine months to make a baby: they must work very fast". Nevertheless, very few "mistakes" happen during this fast work. Obviously there is either an absence of disturbing factors, or very effective control and repair mechanisms at work. The present inventor has accepted the challenge to identify these, and to put them to use in combatting cancer.

The present inventor is of course aware of the fact that there are instances where a fetus develops neuroblastoma, leukemia or teratoma, but these diseases are extremely rare. As the metabolism and development of the mammalian fetus is regulated by the same genes as in the adult mammal, it becomes interesting to determine what conditions or factors, molecular or other, differ between the period spent in utero, and the life post partum.

Additionally, the fast and well-regulated proliferation phase must then be quickly and adequately down-regulated. The similarities and differences between the well-regulated fast proliferation in the embryonal phase and the unregulated, pathological proliferation encountered in various forms of cancer have been the subject of extensive research. A number of relevant articles are listed in the attached list of references, incorporated herein by reference.

Understanding the factors regulating both benign and malignant cell proliferation is crucial for the capability to predict, detect and treat cancer. Important work is being performed in vitro, in cell culture. More specifically, the techniques of in vitro cell, tissue and organ culture is of great importance to pure and applied science, medicine and industry. Amongst others, it is considered a major replacement alternative in animal experimentation. This use poses high requirements on the reliability and repeatability of the experiments.

Cells require a complex environment in order to survive and proliferate in vitro. Therefore, in order to successfully culture cells in vitro, culture medium needs to be added to the cells. Usually, the culture medium contains animal serum as this contains basic components, such as hormones, growth factors, essential elements, proteins, amino acids, nucleic acids, etc. The most common type of serum used for cell growth is fetal bovine serum (FBS), also known as fetal calf serum (FCS). Serum from other species is also available.

FBS is obtained from fetuses harvested in abattoirs from healthy dams fit for human consumption. Sera is also available from other species, such as horse, cat, dog, rabbit, et cetera, and used primarily when cells from said species are cultured. In the cell culture, the serum provides a source of a wide variety of macromolecular proteins, low molecular weight nutrients, carrier proteins for water-insoluble components, and other compounds necessary for in vitro growth of cells, such as hormones and attachment factors. Serum also adds buffering capacity to the medium and binds or neutralizes toxic components. So far, attempts to replace serum entirely with serum-free medium have met only with limited success. Serum must therefore be considered to be a raw material or reagent of crucial importance for research and manufacture within the entire life science sector.

In the serum manufacturing process, whole blood is aseptically collected and allowed to clot. Once the serum has been separated from the clot, it is pooled and frozen. Selected batches are then thawed, tested for endotoxins and hemoglobin content and only the accepted material is pooled and thoroughly blended. The pooled sera is then sterile filtered using a sequence of pre-filters and membrane filters. For example a 0.1 micron sterilizing grade filter or a series of such filters, can be used. After filtration, the serum is aseptically dispensed into bottles ensuring the sterility of the final product.

Using fertilized eggs as growth medium is an alternative to animal sera, used in large scale methods, for example in the production of for example of vaccines, and antibodies, for prophylactic, therapeutic and diagnostic purposes.

There are several manufacturers of animal sera for cell culture purposes, and all take great care to ensure that the products meet high requirements with regard to sterility, purity, and other quality criteria. One manufacturer lists the following properties, shown in Table 1 below:

TABLE 1

Quality control of serum products

Physical and chemical tests:

Electrophoretic pattern, pH, osmolarity, total proteins, albumin, IgG, hemoglobin, globulins Biochemical tests:

Alanine transaminase (ALT), alkaline phosphatase, aspartase aminotransferase (ast), bilirubin - total, bilirubin - direct, blood urea nitrogen (BUN), calcium, chloride, cholesterol, creatinine, creatinine kinase (CK), gamma-glutamyl transferase (GGT), glucose, high density lipoproteins (HDL), low density lipoproteins (LDL), inorganic phosphorous, potassium, sodium, triglycerides (TG), and uric acid Microbiological tests:

Sterility test (bacterial and fungal sterility tests according to current USP)
Mycoplasma contamination (according to CFR)
Viral contamination (according to CFR for bovine viral diarrhea (BVD), infectious bovine rhinotracheitis (IBR), and parainfluenza type 3 (PI3)
Viral antibodies (determination of titer of antibodies to BVD, IBR and PI3)
Endotoxins (Limulus amebocyte lysate (LAL) test using kinetic turbidimetric method)

The manufacturers also test the stability and biological performance, i.e. checking the efficacy of the serum in promoting cell growth. However, as a precaution, manufacturers frequently underline that serum is a biological material, an undefined mixture of components in which the composition varies from one lot to another, and that some cell types are sensitive to variations in serum performance. As a consequence, customers are encouraged to evaluate serum samples using their own culture system and cells. In the meantime, the manufacturer reserves quantities of the specific lots until the testing is complete. In this way, a customer may choose the serum best suited for his particular applications (Product brochure E49/2 07/15 from Biological Industries Israel Beit Haemek Ltd., Kibbutz Beit Haemek, 25115, Israel).

Further, a large range of drugs and reagents used in therapy and diagnosis are currently synthesized using cell culture methods in large scale manufacturing facilities. Cell culture is also widely used in the vaccine industry, as well as in the production of antibodies. Lately, cell culture has also been used in the production of tissues and even organs, for use in reconstructive surgery and transplants. All these uses of serum and serum products involve extremely high requirements on reliability and repeatability.

The present inventor has recognized a need for improving the quality and reliability of cell culture media and cell culture methods. He has also set out to investigate the causative factors behind cancer, aiming at finding new approaches to prevent, alleviate or treat cancer.

SUMMARY

The present inventor has studied the biological roles of two metals, zinc and cadmium, and their behavior, distribution and ratio in the body. One important finding is that while zinc passes through the placenta barrier, into the developing fetus, a healthy placenta will effectively bind cadmium. As a consequence of this finding, the inventor postulates that it is extremely important to analyze and be aware of the concentration of these two metals, and the ration between them, both when studying cancer, and when treating cancer. It is for example important that blood products which are administered to a patient do not contain any cadmium, or as little cadmium as possible. Similarly, it is of great importance to know the concentration of these metals in cell culture media, for example when studying cell proliferation.

Without wishing to be bound by theory, the inventor contemplates that the cancer promoting effect of cadmium is liked to the metal's effect on the tight junctions, the closely associated areas of two cells whose membranes join together forming a virtually impermeable barrier to fluid. This is a type of junctional complex present only in vertebrates. The inventor contemplates that disruption of the tight junction promotes metastasis.

The present inventor has also surprisingly found that the concentration of metals, in particular the concentration of Zn(II), varies significantly in serum products of different batches and from different animal origin. At the same time, the present inventor postulates that the concentration of metals, in particular Zn(II), has a significant influence inter alia on the proliferation of cells cultured in media containing serum products. This makes it important that the concentration of metals, in particular the concentration of Zn(II), is known, and it becomes equally important that the concentration of Zn(II) is adjusted to a desired level.

The term "adjusted" can here mean that the concentration is increased or reduced, depending on the initial level and the desired level. This is relevant for serum products intended to be used as such use in therapy, as well as serum product intended for use in the manufacture of drugs, such as antibodies or vaccines, or reagents, such as reagents used in diagnostic assays and kits, e.g. antibodies. This is also relevant for serum products for use in the culture of cells, tissues or even organs, for use in therapy, e.g. reconstructive surgery or transplants.

One aspect of the invention relates to the importance of knowing the true Zn(II) concentration in a fetal serum product intended for such use. Consequently, one embodiment of the invention concerns a method step in the manufacture of serum products, in particular serum products intended for use in in vitro culture of cells or tissues, wherein the concentration of Zn(II) is determined. Preferably the concentration of Zn(II) in the serum is adjusted to a desired interval, more preferably reduced or increased in correlation to other culture parameters in question.

According to a preferred embodiment, the concentration of Zn(II) is adjusted to an interval of about 50 to about 200 µmol/l in the final serum product. According to an alternative embodiment, the concentration of Zn(II) is adjusted to about 50 µmol/l in the final product.

According to yet another alternative embodiment, the concentration of Zn(II) is adjusted to an interval of less than about 15 µmol/l, preferably less than about 10 µmol/l, more preferably less than about 5 µmol/l in the final serum product.

According to one embodiment, the adjustment of the concentration of Zn(II) is performed by mixing fetal serum of at least two different serum batches having different concentrations of Zn(II) in a ratio such that the final concentration of Zn(II) is in an interval of about 50 to about 200 µmol/l in the final serum product.

According to an embodiment, the adjustment of the concentration of Zn(II) is performed by subjecting fetal serum to a separation method, e.g. ultracentrifugation and removing the formed pellet.

According to an embodiment, freely combinable with all the above embodiments, the fetal serum is fetal serum from a mammal chosen from cattle, pig, horse, goat, cat, dog, and rabbit. According to a specific embodiment, when human serum is involved, this is human umbilical cord serum or serum obtained from healthy donors.

Another aspect of the invention is the surprising finding relating to the significance of exosomes present in fetal serum, their content of Zn(II) and the possibilities it opens for adjusting the Zn(II) content of serum products. Not only are there indications (see the Examples section and the analysis results) that the exosomes and possibly other micro and nano particles in the serum contain the main portion of the Zn(II) present in the serum, there are also indications that exosomes play a significant role in the signaling between cells, and in the proliferation of cells of different origin. It is contemplated that exosomes function as transporters and reservoirs of Zn in the serum, and that this function can be utilized to optimize both the quality of serum products and cell culture conditions in various applications.

The inventor has also found indications that the exosomes are capable of absorbing cadmium, and that the exosomes can be an important carrier of cadmium in blood and serum products. This finding makes it possible to reduce the cadmium content in blood and serum products by removing contaminated exosomes. According to an embodiment, exosomes with a high concentration of cadmium can be removed and replaced by exosomes containing zinc.

Another aspect of the invention relates to products where serum is collected and the exosomes separated, forming a range of products without or with specified concentrations of exosomes, and correspondingly specified, desired concentrations of Zn(II). Preferably serum is collected from different species, which allows the production of species specific products, such as bovine, avian, and human serum products and exosome fractions. A preferred embodiment relates to the collection of umbilical cord blood and the preparation of human serum fractions with specified concentrations of exosomes, and correspondingly different, desired concentrations of Zn(II).

The present inventor has realized that the concentration of exosomes as well as the concentration of Zn(II) needs to be known and preferably adjusted to pre-set desired levels in order to guarantee reliable and consistent result in manufacturing and research applications where fetal serum products are used.

Thus, according to another embodiment, also freely combinable with all the above embodiments, the concentration of exosomes in the serum is determined, and the concentration in the final product is adjusted to a value within a desired interval.

Yet another embodiment, also freely combinable with all the above embodiments, makes available a method step in the manufacture or the preparation of a fetal serum product based on fetal serum of a specific species, wherein the diameter of the exosomes is determined, and/or the concentration of Zn(II) in the exosomes in serum from said specific species is determined, whereupon the concentration of Zn(II) in the final product is adjusted, i.e. increased or reduced, to a value within a desired interval. This can be done by separating and removing a Zn(II) containing fraction, e.g. an exosome fraction, or by adding such fraction, in order to achieve the desired concentration.

Similarly, the concentration of cadmium can be reduced by removing contaminated exosomes, and replacing them with healthy, non-contaminated exosomes.

An important aspect of the invention is thus the provision of new and improved fetal serum products, including human umbilical cord serum or healthy donor serum, inter alia a fetal serum product manufactured according to a method or methods including one or more of the steps set out in the above embodiments.

One example is a fetal serum product having a concentration of Zn(II) adjusted to an interval of about 50-about 200 µmol/l. Another example is a fetal serum product having a concentration of Zn(II) adjusted to about 50 µmol/l. A preferred example is a fetal serum product having a concentration of Zn(II) adjusted to an interval of less than about 15 µmol/l, preferably less than about 10 µmol/l, more preferably less than about 5 µmol/l in the final product.

An important aspect is that the concentration of Zn(II) should be determined and known before the product is used. One embodiment therefore relates to a fetal serum product, preferably but not necessarily manufactured using one or more of the above steps, wherein the concentration of Zn(II) in said product has been determined and is indicated on the package or in the accompanying product data sheet.

Yet another aspect of the invention relates to methods for cell or tissue culture, regardless if the cell or tissue culture is part of a production method, a diagnostic method, therapy or research. One embodiment of this aspect is a method for in vitro cell or tissue culture using a culture medium containing a fetal serum product, wherein the concentration of Zn(II) in the culture medium is determined, and adjusted to a desired level.

In the above embodiment, preferably the cells to be cultured are human cells, and the concentration of Zn(II) in the culture medium is adjusted to a value in the interval of 50-about 200 µmol/l, more preferably the concentration of Zn(II) in the culture medium is adjusted to about 50 µmol/l. More preferably the concentration of Zn(II) in the culture medium is adjusted to a value within an interval of less than about 15 µmol/l, preferably less than about 10 µmol/l, more preferably less than about 5 µmol/l in the final product.

Another aspect of the invention relates to methods for in vitro cell or tissue culture using a culture medium containing a fetal serum product, wherein the concentration of Zn(II) in the culture medium is determined, adjusted to a selected level, and maintained at said level during the duration of the cell or tissue culture and/or when repeating said culture.

Yet another aspect of the invention concerns avian serum products, and in particular egg white and egg yolk. The present inventor has found that eggs contain higher amounts of Zn(II) than mammalian serum. The concentration of Zn(II) in egg yolk can be in the interval of 50-70 micro molar. The inventor postulates that it is of considerable significance that the concentration of Zn(II) is known in order to ensure repeatability of the culture methods where avian serum or egg products are used. Further, it is also preferred that the concentration of Zn(II) is adjusted to a desired level also in avian serum and/or eggs. This can be achieved for example by the feed, or by adding a species specific Zn(II) containing fraction to an avian serum product or to eggs.

An embodiment of the invention therefore relates to avian serum products manufactured according to the methods or method steps disclosed herein, mutatis mutandis, i.e. with necessary modifications.

One embodiment is thus an avian serum product having a concentration of Zn(II) adjusted to an interval of about 50-about 200 μmol/l. Preferably said avian serum product has a concentration of Zn(II) adjusted to about 50 μmol/l.

According to a preferred embodiment, the avian serum product has a concentration of Zn(II) adjusted to an interval of less than about 15 μmol/l, preferably less than about 10 μmol/l, more preferably less than about 5 μmol/l in the final product.

A particular embodiment is an avian serum product wherein the concentration of Zn(II) in said product has been determined and is indicated on the package or in the accompanying product data sheet.

Another embodiment of said aspect is a method for in vitro cell or tissue culture using a culture medium containing an avian serum product, wherein the concentration of Zn(II) in the culture medium is determined, and adjusted to a desired level. Preferably the concentration of Zn(II) in the culture medium is adjusted to a value in the interval of 50-about 200 μmol/l. More preferably the concentration of Zn(II) in the culture medium is adjusted to about 50 μmol/l.

Yet another embodiment is the use of avian serum and/or eggs in cell and/or tissue culture, or in the manufacture of antibodies and vaccines, including a method step wherein Zn(II) enriched serum or a serum fraction is added to a fertilized egg using known methods for inoculating eggs. This Zn(II) enriched serum or a serum fraction is species specific, i.e. when added to hen eggs, hen serum is used, and when added to duck eggs, duck serum is used. The Zn(II) concentration of the enriched serum or fraction is determined and the serum or fraction is also subjected to necessary quality control, as known to persons skilled in the art.

Further, according to an embodiment freely combinable with the above aspects and embodiments, the cells to be cultured are human cells, and the concentration of Zn(II) in the culture medium is adjusted to a value within an interval of less than about 15 μmol/l, preferably less than about 10 μmol/l, more preferably less than about 5 μmol/l in the final product/l. In the case of eggs, the concentration of Zn(II) can be influenced by adjusting the composition and amount of feed given to the birds, e.g. hens or ducks.

Another aspect is a novel method for in vitro cell or tissue culture using a culture medium containing an avian serum product, characterized in that that the concentration of Zn(II) in the culture medium is determined, adjusted to a selected level, and maintained at said level during the duration of the culture and/or when repeating said culture.

Another embodiment is the use of species specific Zn(II) enriched sera or fractions, e.g. species specific exosome fractions in cell, tissue and organ cultures. Such species specific sera or serum fractions can be manufactured in cell culture under species specific conditions.

Another object of the present invention is to provide methods for the prevention, treatment, and alleviation of cancer in mammalian subjects, based on the inventor's understanding of the role of cadmium in the induction of cancer.

This and other objects are achieved by the aspects and embodiments defined in the independent claims, incorporated herein by reference. Further advantageous embodiments have been specified in the dependent claims, incorporated herein by reference.

SHORT DESCRIPTION OF THE FIGURES

Different aspects and embodiments will be disclosed in closer detail in the following description, examples and claims, with reference to the attached figures in which:

DESCRIPTION OF EMBODIMENTS

Before the present invention is described, it is to be understood that the terminology employed herein is used for the purpose of describing particular embodiments only and is not intended to be limiting, since the scope of the present invention will be limited only by the appended claims and equivalents thereof.

It must be noted that, as used in this specification and the appended claims, the singular forms "a," "an," and "the" include plural referents unless the context clearly dictates otherwise.

Also, the term "about" is used to indicate a deviation of +/−2% of the given value, preferably +/−5%, and most preferably +/−10% of the numeric values, where applicable.

The term "fetal serum products" is used to indicate both fetal serum as such, when marketed as a reagent or substrate for use in production, diagnosis, therapy or in research applications, as well as products for such use, comprising fetal serum.

In relation to humans, the source of serum and exosomes is preferably umbilical cord blood, but is it not excluded that blood products from healthy donors can be used.

The general understanding until now is that fetal bovine serum (fetal calf serum) is the most suitable serum-supplement for in vitro cell culture of eukaryotic cells and tissues. This is due to it having a very low level of antibodies and containing more growth factors, allowing for versatility in many different cell culture applications. The globular protein, bovine serum albumin (BSA), is a major component of fetal bovine serum. The rich variety of proteins in fetal bovine serum maintains cultured cells in a medium in which they can survive, grow, and divide.

Apparently other properties of fetal serum and avian serum including egg products have not yet been subject to closer scrutiny. The present inventor has however found that while the normal concentration of zinc in the form of Zn(II) in human serum ranges from about 10 to about 20 μmol/l (some sources report a range of 9 to 18 μmol/l, others a range of 6-14 μmol/l) the concentration in animal sera, including fetal bovine serum, varies within a significantly wider interval. Analyses commissioned by the present inventor have revealed Zn(II) concentrations ranging from 0.5 µmol/l to 91.4 µmol/l.

The present inventor has also investigated the concentration of cadmium in serum samples and found that the concentration was below the detection limit of the methods used. As there are strong indications that cadmium is a contributory factor in the development of cancer, the inventor postulates that it is important that the concentration of cadmium in culture media is known, and preferably controlled, i.e. adjusted and/or maintained to/at a desired level, as changes in concentration are likely to influence the proliferation of the cells and/or tissue in the culture.

Cadmium is referred to as a non essential element, together with mercury and lead, as these lack essential nutrient properties unlike other transition metals such as copper, zinc, cobalt, manganese, and molybdenum. These metals are generally considered as toxic to mammals, and they frequently imitate the action of an essential element in the body, interfering with the metabolic processes, and causing illness. According to WHO information, it is established that cadmium exerts toxic effects on the kidney, the skeletal and the respiratory systems, and that it is classified as a human carcinogen. Cadmium is generally present in the environment at low levels. However, human activity has greatly increased those levels.

Cadmium can travel long distances from the source of emission by atmospheric transfer. It is readily accumulated in many organisms, notably mollusks and crustaceans. Lower concentrations are found in vegetables, cereals and starchy roots. Human exposure occurs mainly from consumption of contaminated food, active and passive inhalation of tobacco smoke, and inhalation by workers in the non-ferrous metal industry. The WHO calls for national, regional and global actions to decrease global environmental cadmium releases and reduce occupational and environmental exposure.

The most dangerous characteristic of cadmium is that it accumulates in the mammalian body, mainly in the liver and kidney. The concentrations of cadmium in the liver and kidney are comparable after short-term exposure, but the kidney concentration tends to exceed the liver concentration in the case of long-term exposure.

Reference levels for cadmium indicates that healthy non-smokers will have less than about 5 µmol/l cadmium in their blood. This has been confirmed by tests commissioned by the inventor, showing concentrations of 5.3 µmol/l. The cadmium concentration for habitual smokers is generally much higher, but frequently less than about 18 µmol/l. Acute toxicity is observed at concentrations around 50 µng/ml.

Based on his experimental work, the present inventor makes available a method for use in the prevention, treatment, and/or alleviation of cancer in a mammal, wherein said mammal is subjected to a treatment reducing the amount of cadmium and/or changing the proportion of cadmium in relation to zinc in the body of said mammal. The significance of this approach is supported by the inventor's finding that the placenta prevents cadmium from passing into the fetus, ensuring the extremely rapid, effective and simultaneously practically error free proliferation and differentiation of cells that takes place during the gestation period.

The above method can be applied to the prevention of metastasis and recurrence of cancer, and can preferably be performed in combination with surgical removal of the tumor, preferably initiated already before the surgical procedure and continued after said surgical removal of the tumor.

The above method can also be applied in combination with surgical removal of the tumor and the administration of one or more cytostatic drug or drugs.

Similarly, the method according to the above embodiments can be performed in combination with radiation therapy.

According to another embodiment, freely combinable with the above embodiments, the treatment further involves the administration of a non-toxic dose of a metal chosen from iron, selenium and zinc, preferably zinc.

According to another embodiment, freely combinable with the above embodiments, the treatment further involves a reduction of the amount of cadmium or change of the proportion of cadmium in relation to zinc, wherein said reduction or change is performed by means of blood transfusion.

As an alternative or as a complement to blood transfusion, isolated exosomes or an enriched exosome fraction can be used. The present inventor has experimentally shown that exosomes can absorb zinc from surrounding serum. Based on this, it is suggested that the zinc content of exosomes is increased by adding zinc to serum comprising exosomes, and then separating an exosome fraction "loaded" with zinc.

In this context it is very important to mention that smokers have increased concentrations of cadmium in their blood, and that smokers therefore should be disqualified from donating blood, or at least that blood from smokers should never be given to cancer patients. Accordingly, the present inventor suggests that blood donors are asked to report their smoking habits, and that blood obtained from smoking donors is not used at all, used with restrictions, or treated so that the cadmium is removed or the level of cadmium is reduced. In the alternative, it would be advantageous if donated blood was screened for cadmium content, similarly as is now done for HIV and hepatitis C, so that it can be ensured that patients suffering from cancer, or patients with impaired general health, suffering from or susceptible to disease, will not receive blood products which risk introducing cadmium in their system.

According to another embodiment, freely combinable with the above embodiments, the reduction of the amount of cadmium or change of the proportion of cadmium in relation to zinc is performed by means of extracorporeal dialysis.

The method according to the above embodiment, wherein the reduction of the amount of cadmium or change of the proportion of cadmium in relation to zinc is performed by means of dietary adjustments.

An advantage of the suggested approach is that the treatment is minimally invasive, and—in the case of zinc supplementation or dietary adjustments—relatively safe and easy to implement. An additional advantage is that the suggested approach relies on the inherent capability of repair and recovery of the mammalian body, which is demonstrated by the practically flawless differentiation and proliferation of cells during fetal development. Other advantages will be evident to a person skilled in the art upon study of the description, examples and claims.

In his experimental work, the inventor also found that an exosome fraction or pellet can be isolated from the serum by ultracentrifugation. This opens possibilities not only to reduce the concentration of Zn(II) but also to increase the same. The exosome pellet can be re-suspended and used to adjust the Zn(II) concentration for example by adding exosomes to fetal or avian serum, or to a fertilized egg or to egg products.

In the case of vaccine production in fertilized eggs, an exosome fraction rich in Zn(II) can be introduced into the egg by micro injection or other known methods, simultaneously with or in association with the inoculation of the egg with the antigen. For the specific avian use, and for addition to eggs, the exosome fraction is prepared from blood from a bird or birds of the same species. This opens possibilities to optimize the production of antibodies in eggs, and also to adjust or optimize vaccine production.

A first aspect of the invention relates to the importance of knowing the true Zn(II) concentration in a fetal serum product intended for use in medicine, including diagnosis and therapy, as well as in the production of reagents and agents for use in diagnosis and therapy, and in research.

Consequently, one embodiment of the invention concerns a method step in the manufacture of serum products, in particular serum products intended for use in in vitro culture of mammalian cells or tissues, wherein the concentration of Zn(II) is determined. Preferably the concentration of Zn(II) in the serum is adjusted to a desired interval, more preferably significantly reduced.

According to a preferred embodiment, the concentration of Zn(II) is adjusted to an interval of about 10 to about 500 µmol/l, preferably about 50 to about 200 µmol/l in the final serum product. According to an alternative embodiment, the concentration of Zn(II) is adjusted to about 50 µmol/l in the final product.

According to yet another alternative embodiment, the concentration of Zn(II) is adjusted to an interval of less than about 15 µmol/l, preferably less than about 10 µmol/l, more preferably less than about 5 µmol/l in the final serum product.

According to an embodiment, the adjustment of the concentration of Zn(II) is performed by mixing fetal serum of at least two different serum batches having different concentrations of Zn(II) in a ratio such that the final concentration of Zn(II) is in an interval of about 50 to about 200 µmol/l in the final serum product.

According to an embodiment, the adjustment of the concentration of Zn(II) is performed by subjecting fetal serum to ultracentrifugation and removing the formed pellet, or using other separation methods as applicable.

According to an embodiment, freely combinable with all the above embodiments, the fetal serum is fetal serum from a mammal chosen from cattle, pig, horse, goat, cat, dog, and rabbit. The currently most frequently used fetal serum is bovine fetal serum (BFS) also known as fetal calf serum (FCS)

Another aspect of the invention relates to the realization of the significance of exosomes present in fetal serum. Not only are there indications (see the Examples section) that the exosomes and possibly other micro and nano particles in the serum contain the main portion of the Zn(II) present in the serum, there are also indications that exosomes play a significant role in the signaling between cells, and in the proliferation of cells of different origin.

The present inventor has realized that the concentration of exosomes as well as the concentration of Zn(II) needs to be known and preferably adjusted to pre-set desired levels in order to guarantee reliable and consistent result in manufacturing and research applications where fetal serum products are used.

Thus, according to another embodiment, also freely combinable with all the above embodiments, the concentration of exosomes in the serum is determined, and the concentration in the final product is adjusted to a value within a desired interval.

Yet another embodiment, also freely combinable with all the above embodiments, makes available a method step in the manufacture or the preparation of a fetal serum product based on fetal serum of a specific species, wherein the diameter of the exosomes is determined, and/or the concentration of Zn(II) in the exosomes in serum from said specific species is determined, whereupon the concentration of Zn(II) in the final product is adjusted a value within a desired interval.

An important aspect of the invention is thus the provision of new and improved fetal serum products, inter alia a fetal serum product manufactured according to a method or methods including one or more of the steps set out in the above embodiments.

One example is a fetal serum product having a concentration of Zn(II) adjusted to an interval of about 50-about 200 µmol/l. Another example is a fetal serum product having a concentration of Zn(II) adjusted to about 50 µmol/l. A preferred example is a fetal serum product having a concentration of Zn(II) adjusted to an interval of less than about 15 µmol/l, preferably less than about 10 µmol/l, more preferably less than about 5 µmol/l in the final product.

An important aspect is that the concentration of Zn(II) should be determined and known before the product is used. One embodiment therefore relates to a fetal serum product, preferably but not necessarily manufactured using one or more of the above steps, wherein the concentration of Zn(II) in said product is indicated on the package or in the accompanying product data sheet.

Yet another aspect of the invention relates to methods for cell or tissue culture, regardless if the cell or tissue culture is part of a production method, a diagnostic method, therapy or research. One embodiment of this aspect is a method for in vitro cell or tissue culture using a culture medium containing a fetal serum product, wherein the concentration of Zn(II) in the culture medium is determined, and adjusted to a desired level.

In the above embodiment, preferably the cells to be cultured are human cells, and the concentration of Zn(II) in the culture medium is adjusted to a value in the interval of 50-about 200 µmol/l, more preferably the concentration of Zn(II) in the culture medium is adjusted to about 50 µmol/l. More preferably the concentration of Zn(II) in the culture medium is adjusted to a value within an interval of less than about 15 µmol/l, preferably less than about 10 µmol/l, more preferably less than about 5 µmol/l in the final product/l.

Another aspect of the invention relates to methods for in vitro cell or tissue culture using a culture medium containing a fetal serum product, wherein the concentration of Zn(II) in the culture medium is determined, adjusted to a selected level, and maintained at said level during the duration of the cell or tissue culture and/or when repeating said culture.

Yet another aspect of the invention concerns avian serum products, and in particular egg white and egg yolk. The present inventor has found that eggs contain higher amounts of Zn(II) than mammalian serum. The concentration of Zn(II) in egg yolk can be in the interval of 50-70 micro molar. The inventor postulates that it is of considerable significance that the concentration of Zn(II) is known in order to ensure repeatability of the culture methods where avian serum or egg products are used. Further, it is also preferred that the concentration of Zn(II) is adjusted to a desired level.

An embodiment of the invention therefore relates to avian serum products manufactured according to the methods or method steps disclosed herein, mutatis mutandis, i.e. with necessary modifications.

One embodiment is thus an avian serum product having a concentration of Zn(II) adjusted to an interval of about 50-about 200 µmol/l. Preferably said avian serum product has a concentration of Zn(II) adjusted to about 50 µmol/l.

According to a preferred embodiment, the avian serum product has a concentration of Zn(II) adjusted to an interval of less than about 15 µmol/l, preferably less than about 10 µmol/l, more preferably less than about 5 µmol/l in the final product.

A particular embodiment is an avian serum product wherein the concentration of Zn(II) in said product is indicated on the package or in the accompanying product data sheet.

Another embodiment of said aspect is a method for in vitro cell or tissue culture using a culture medium containing an avian serum product, wherein the concentration of Zn(II) in the culture medium is determined, and adjusted to a desired level. Preferably the concentration of Zn(II) in the culture medium is adjusted to a value in the interval of 50-about 200 µmol/l. More preferably the concentration of Zn(II) in the culture medium is adjusted to about 50 µmol/l.

Further, according to an embodiment freely combinable with the above aspects and embodiments, the cells to be cultured are human cells, and the concentration of Zn(II) in the culture medium is adjusted to a value within an interval of less than about 15 µmol/l, preferably less than about 10 µmol/l, more preferably less than about 5 µmol/l in the final product/l. In the case of eggs, the concentration of Zn(II) can be influenced by adjusting the composition and amount of feed given to the birds, e.g. hens or ducks.

Another aspect is a novel method for in vitro cell or tissue culture using a culture medium containing an avian serum product, wherein the concentration of Zn(II) in the culture medium is determined, adjusted to a selected level, and maintained at said level during the duration of the culture and/or when repeating said culture.

Interestingly, when embryonic stem cells are cultivated in the absence of cadmium, rapid growth and differentiation is achieved without any signs of tumorigenesis. However, when immortalized cell lines, tumor cell lines, are cultivated, this is conventionally done in the presence of 10% fetal bovine serum, which has now been shown—by the inventor—to contain varying amounts of cadmium.

In the light of these results, it seems very plausible that the capacity of the placenta to block the cadmium ions from passing into embryonal tissue has significant importance. The present inventor is not in position to definitely postulate which are the most deleterious reactions in which cadmium is a key factor, but it is contemplated that the cadmium ion disturbs the balance between the action of phosphatases and kinases, which together regulate the phosphorylation state of many important signaling molecules and cellular processes implicated in cell growth, cellular differentiation, mitotic cycles, oncogenic transformation and receptor endocytosis.

Another theory proposed by the present inventor is that cadmium takes the place of calcium, in reactions involving cadhedrins, a group of transmembrane proteins known to play important roles in cell adhesion, the separation of different tissue layers and cell migration. Interestingly, malfunctioning of the epithelial cadhedrin-catenin complex has been associated with tumor metastasis. The inventor speculates that it is the similarity between the ion radius of the Ca2+ ion (114 m) and the Cd2+ ion (109 pm) that makes this possible.

The inventor contemplates that the above effects directly influence and disturb the function of the tight junction, for example making it possible for cancerous cells to leave diseased tissue, travel in the blood stream and lymphatic system, and entering healthy tissues. In this case, increased concentration of cadmium could directly promote metastasis of cancer.

Another theory suggested by the present inventor is that the presence of the metals cadmium and zinc, their concentrations and the ratio between them, directly influences the functioning of the enzymes involved in DNA replication as well as in the enzymatic correction of replication errors.

EXAMPLES

Example 1. Analysis of Zn(II) Concentration in Sera of Different Origin

The present inventor has commissioned analyses of different batches of sera, and also sera from different animals. These analysis of different batches of FBS has revealed significant variations in the concentration of Zn(II) between batches. The analysis of sera from different animals has revealed significant variations between animals.

The analyses were performed at an accredited laboratory, using atomic absorption spectroscopy (AAS) and standard samples obtained from Perkin-Elmer (Norwalk, Conn., USA). The results are shown in Table 2.

TABLE 2

Concentration of Zn(II) in serum samples

| Serum Sample | Concentration of Zn µmol/l |
|---|---|
| FBS (USA) 1 | 56.1 |
| FBS (USA) 2 | 91.4 |
| FBS inactivated | 47.5 |
| FBS (Non-US) (Sigma Lot No. 103 M 3396/F 7524) | 26 |
| FBS | 37.0 |
| FBS (US) (Sigma Lot No. 074 M 3328) | 33 |
| FBS | 60.9 |
| Newborn Calf Serum (US) (Sigma N-4762 14 A 316) | 11 |
| Iron-fortified Calf Serum from Formula fed animals (US) Sample 1 (Sigma C 8066 11 M 026) | 22 |
| Iron-fortified Calf Serum from Formula fed animals (US) Sample 2 (Sigma C 8066 11 M 026) | 23 |
| Newborn calf serum (NZ) (GIBCO 16010 NBCS Ref. No. 1060??-167) | 17 |
| Bovine Serum (NZ) (GIBCO Lot. No. 137 2691/26170 035) | 17 |
| Newborn Calf Serum (NZ) Heat inactivated (GIBCO Ref: 26010-066, Lot. No. 1169982) | 18 |
| Bovine Serum (NZ) (GIBCO Ref: 16170-86, Lot. No. 1610982) | 14 |
| FBS (ZA) (GIBCO REF 1o 270-098, Lot No. 42 F 035 1 K) | 24 (34) |
| FBS (USA) | 27 |

TABLE 2-continued

Concentration of Zn(II) in serum samples

| Serum Sample | Concentration of Zn μmol/l |
|---|---|
| GIBCO Ref. 26140 087, Lot. 1680 777) FBS (AU) | 25.8 |
| (GIBCO Ref. 10099-133, Lot. No. 1633098) FBS (AU) Heat-inactivated | 25.7 |
| (GIBCO Ref. 10100-139 Lot No. 1688877 S) FBS (US) 3 | 56.1 |
| Goat serum (NZ) | 12.2 |
| GIBCO Ref. 16210-064, Lot No. 1517965) Rabbit serum (US) | 27.8 |
| (GIBCO Ref. 16120-099, Lot. No. 1705973) Horse serum (NZ) | 15.8 (15.6) |
| (GIBCO Ref. 16050-130, Lot No. 1486538) Chicken serum (NZ) | 78.2 |
| Porcine serum (NZ) Ref. 26250-084, Lot No. 161 4268 | 22.1 |
| Lamb serum (NZ) (GIBCO Ref. 16070-096, Lot No. 1517956) | 15.6 |

In total, the analysis show that there are indeed considerable variations in the concentration of Zn(II) in serum of different origin, both geographical origin, and from different animal species. Serum and in particular fetal calf serum is a standard ingredient in cell culture, frequently added in an amount of 10% to the culture medium. Nevertheless, it is very seldom if ever that one sees an indication of which serum has been used, or any information about the properties of this serum, for example with regard to the concentration of metal ions.

As the Zn(II) ion has a fundamental role in the cell metabolism, the present inventor concludes that it is of considerable significance that the concentration of Zn(II) is known, and adjusted to a known range. The present inventor suggests that the variation in the concentration of Zn(II) is a considerable source of error both in experiments and in the production of biopharmaceuticals using serum supplemented growth media. It is consequently preferred that the concentration of Zn(II) is adjusted so, that the final concentration in the cell culture medium falls within the normal concentration of zinc in the form of Zn(II) in human serum, i.e. in a range from about 10 to about 20 μmol/l. Preferably the same concentration is ascertained in all experiments, and in all production batches, in order to guarantee reliable results and an even quality of products.

Example 2. Analysis of Cd Concentration in Fetal Serum Samples

The inventor also commissioned the analysis of cadmium in a number of serum samples. To the best of his knowledge, cadmium has no known beneficial function in the human body. There however exists epidemiological evidence showing a significant association between cadmium in human serum, and cancer.

The concentration of cadmium was determined at an accredited laboratory (VITA Laboratorio, VITA-Terveyspalvelut, Helsinki, Finland), using standard procedures and an atomic absorption spectroscopy (AAS) apparatus from Perkin-Elmer (Norwalk, Conn., USA). The results indicate that fetal serum is free of cadmium or only contains cadmium in levels below the detection limit of the analysis method, here 4.5 μmol/l. The results are shown in Table 3.

TABLE 3

Comparison of Zn(II) and Cd concentration in serum samples

| | Concentration of Zn(II) and Cd | |
|---|---|---|
| Sample ID | Zn(II) μmol/l | Cd nmol/l |
| 2 | 33 | <4.5 |
| 3 | 46 | <4.5 |
| 12 | 34 | <4.4 |
| 13 | 34 | <4.4 |
| 14 | 74 | <4.5 |
| 15 | 44 | <4.5 |

It is generally held that a non-smoker who has not been exposed to cadmium, should exhibit concentrations below 5 nmol/l or less. A smoker will exhibit higher concentrations but less than 18 nmol/l. 50 nmol/l is a threshold at which medical treatment needs to be initiated (information supplied by the analyzing company, VITA Laboratorio).

The above result confirm the threshold for healthy, non-smoking individuals. It remains to analyze the blood of habitual smokers, and it would be of interest to see how the concentration of cadmium changes with time, in order to determine for example for how long a person should be disqualified as a blood donor after having stopped smoking.

The experiments also show that it is feasible to screen donor blood with regard to the content of cadmium, a procedure that the present inventor strongly advocates.

Example 3. Separation of Particles from Sera of Different Origin, First Trial

The present inventor also commissioned a study where cell free serum samples were subjected to ultracentrifugation. The study was performed at VTT Technical Research Centre of Finland Ltd, Espoo, Finland in November 2015. An ultracentrifuge (Beckman Optima™ LE-BOK) was used according to the manufacturer's instructions. The objective of the study was to test if particles with a diameter less than 200 nm (0.2 μm) could be separated from cell free serum samples using ultracentrifugation.

A total of 8 samples were supplied in duplicate, and stored at −20° C. according to the inventor's instructions. A stabilizing reagent (DTT, DL-dithiothreitol) was also supplied by the inventor, and stored at +4° C. The samples were ultracentrifuged at 150 000×g for 20 h at +4° C. One test tube broke during the ultracentrifugation, but with exception for this tube, the test showed that a pellet was formed in all the test tubes. It was noted that in some samples, two pellets were formed, one that was described as "loose" and another, described as glue-like and difficult to dissolve.

Example 4. Separation of Particles from Sera of Different Origin, Second Trial

The present inventor commissioned a second study where cell free serum samples were subjected to ultracentrifugation. The study was performed at VTT Technical Research Centre of Finland Ltd, Espoo, Finland in December 2015. An ultracentrifuge (Beckman Optima™ LE-BOK) was used according to the manufacturer's instructions. The objective of the study was to test if particles with a diameter less than 200 nm (0.2 µm) could be separated from cell free serum using ultracentrifugation.

A total of 8 samples were supplied in duplicate, and stored at −20° C. according to the inventor's instructions. A stabilizing reagent (DTT, DL-dithiothreitol) was also supplied by the inventor, and stored at +4° C.

Four serum samples were thawed on ice, and the volume measured. Each sample was divided in two portions of equal volume, and diluted with 1× PBS to a final volume of 10 ml. The samples were then filtered using 0.2 µm syringe filters supplied by the inventor.

In a first test run, one portion of each sample was transferred to individual ultracentrifuge tubes. In a second test run, the samples were treated with DTT according to the inventor's instructions prior to ultracentrifugation. All samples were treated by ultra centrifuging at 150 000× g for 20 h at +4° C. A pellet could be detected in all tubes.

In the first test run, a loose pellet was seen in all samples, and in one sample an additional, small and denser pellet was observed. The supernatants were collected from each sample, taking great care not to include any of the pellet. DTT was added to the pellets, and the samples were incubated in 37° C. and vortexed every two minutes. During this treatment, the samples formed a gel. This gel was however dissolved by the addition of 1×PBS to a total volume of 10 ml for each sample. The re-suspended pellets were centrifuged once more, at 150 000× g for 1 h and at a temperature of 30–37° C. There were problems reaching the desired temperature of 37° C. until the later part of the centrifugation time (1 h). In each sample, the second centrifugation resulted in a translucent, solid pellet with a faint red color, and none of the loose pellets reported in Examples 2 and 3 above.

In the second test run, subjected to ultracentrifugation using the same conditions, the resulting pellets had a different appearance. They were larger and appeared to consist of two layers, with an upper, larger and looser pellet, and a lower reddish and hard pellet.

In both test runs, there were difficulties in dissolving the hard pellets, so these were transferred to test tubes supplied by the inventor using a shortened 5 ml pipette tip and possibly remaining pellet fragments were collected with a sterile loop. According to the inventor's instructions, 2 drops of 65% nitric acid was added to each tube to promote dissolution. The samples were returned to the inventor for further analysis.

Example 5. Analysis of Exosomes Isolated from Fetal Calf Serum Samples

The pellets obtained in Examples 3 and 4 are washed in PBS and their content of exosomes can be analyzed qualitatively or quantitatively using methods known in the art, e.g. using flow cytometry analysis (FACS), transmission electron microscopy (TEM) analysis, immunogold staining, or NanoSight LM10 (NanoSight Ltd) analysis. Similarly, the concentration of exosomes in fetal serum can be determined by methods known to a skilled person. The samples are preferably subjected to a filtration pre-treatment removing larger particles.

Example 6. Analysis of Zn(II) Concentration

The pellets obtained in Examples 2 and 3 were washed in PBS and the Zn(II) concentration measured by atomic absorption spectrometry using a Perkin Elmer Atomic Absorption apparatus (AAS). The results are shown in Table 4 below:

TABLE 4

Concentration of Zn(II) in samples of serum before and after ultracentrifugation

| Sample ID | Concentration of Zn(II) in µmol/l Type of sample | | |
|---|---|---|---|
| | Serum | Pellet | Supernatant |
| 12 | 43.0 | | |
| 26 | 53.1 | | |
| 27 | 53.4 | | |
| 201 | 48.4 | | |
| 12/1 | | 39 | 1.3 |
| 26/1 | | 50 | 0.4 |
| 27/1 | | 50.1 | 0.7 |
| 201/1 | | 45.2 | 1.4 |
| 12/2 | | 41.5 | 0.5 |
| 26/2 | | 52 | 0.0 |
| 27/2 | | 52.1 | 1.0 |
| 201/2 | | 47.1 | 0.0 |

The analysis shows that the ultracentrifugation was successful in reducing or in some samples, eliminating Zn(II) from the supernatant.

The above examples indicate that Zn(II) is contained in the exosomes present in cell free serum, and also that the concentration of Zn(II) in serum can be significantly reduced or even eliminated using ultracentrifugation or possibly other separation methods. In the majority of the tests, the concentration of Zn(II) in the supernatant was reduced to about 1 µmol/l or less.

The general understanding has hitherto been that metals in serum are bound to albumin, but the current preliminary experiments indicate that at least a portion of the Zn(II) is bound to particulate matter, e.g. exosomes, in serum, and that it can be concentrated and removed for example by ultracentrifugation.

Figure 1:
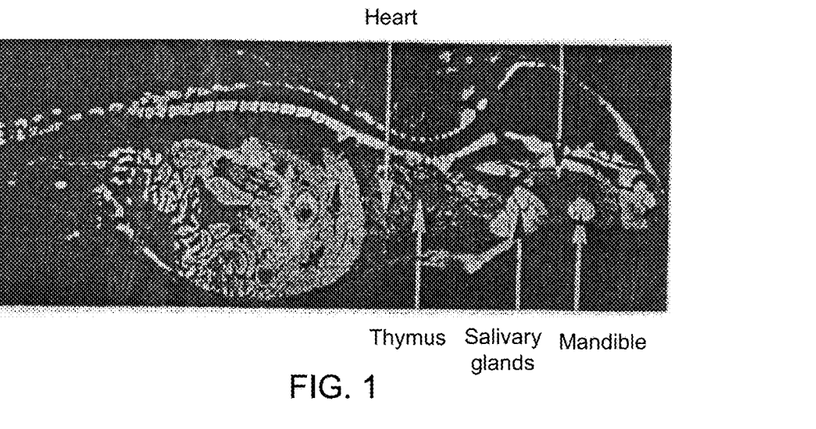
FIG. 1 shows an autoradiograph image of a pregnant mouse, showing the distribution of the radioactive zinc isotope $^{65}Zn$. The white dots in the embryonal sack indicate an enrichment of the isotope. This proves that zinc is capable of passing through the placenta.
Figure 2:
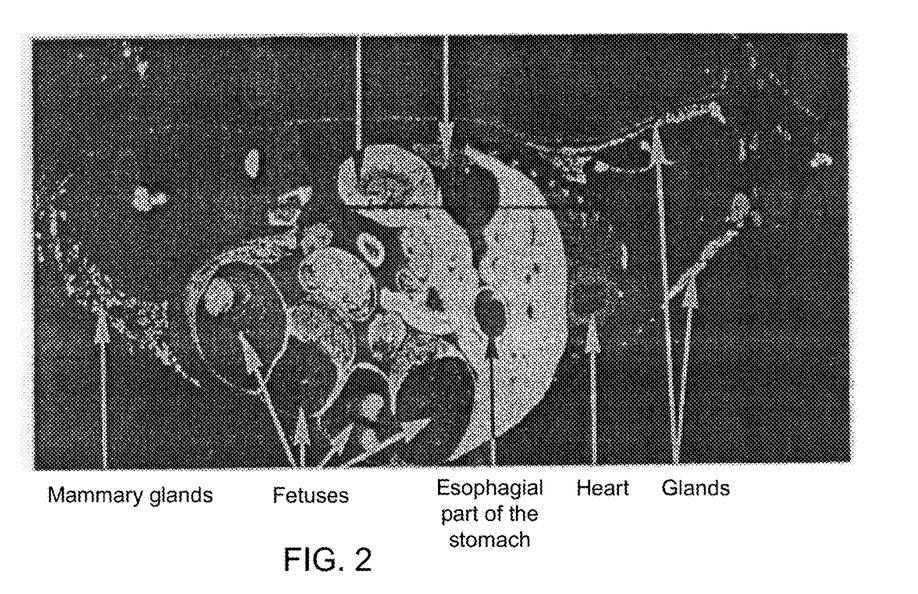
FIG. 2 shows a detailed view, focusing on the uterus containing multiple fetuses. Again, an enrichment of $^{65}Zn$ can be seen.
Figure 3:
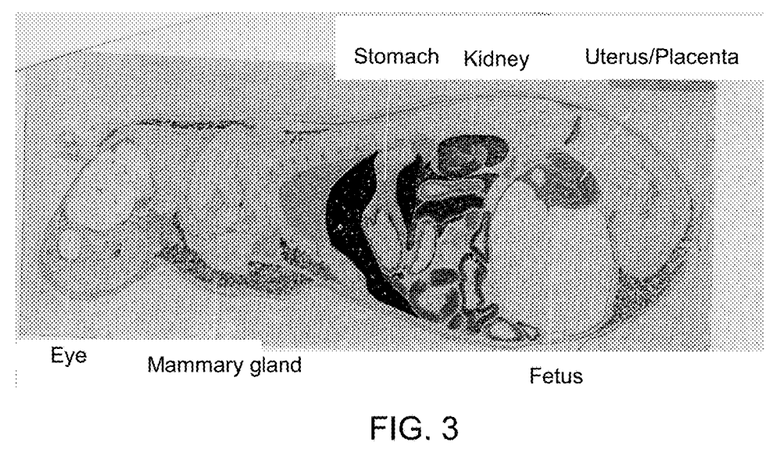
FIG. 3 shows another autoradiograph image of a pregnant mouse that has been subjected to the radioactive cadmium isotope $^{109}Cd$. In this picture, the enrichment of cadmium is shown as black. It can be seen that the cadmium isotope is enriched in the liver and kidney, and to some extent in placental tissue. However, no cadmium has passed through the placenta into the fetus.

Example 7. Whole Body Autoradiography Investigating the Enrichment of Cd and Zn Isotopes The present inventor commissioned studies where the function of the placenta was investigated using radioactive isotopes of cadmium and zinc. Pregnant female mice were injected intravenously with 8 µc of $^{109}CdCl_2$ obtained from Philips Ltd., Eindhoven, Holland. The injection of isotope was made into the tail vein according to standard practice. The mice were injected so that the day of sacrifice coincided approximately with the 18$^{th}$ day after conception, determined by the presence of a vaginal plug after mating. The mice were sacrificed under ether anesthesia by immersion in a mixture of acetone and liquid carbon dioxide (about −80 C). The mice were then sagittally sectioned in a cold room at −10 C according to standard practice, and the sections obtained were affixed to cellulose tape.

Each section was then apposed to X-ray film together with an isotope reference standard. The sections and films were kept at −10 C until exposure was complete. The determination of the order of cadmium and zinc concentration in different organs was made through densitometric comparison of the autoradiographic exposure caused by the organs, compared to the reference standard.

The autoradiography studies showed a significant difference in the behavior of these two metals. While Zn passed through the placenta and was enriched in the fetal tissue, Cd did not pass the placental barrier. The mechanism behind this is not fully understood, but the present inventor contemplates that metallothionein proteins have an important function in binding cadmium and preventing it from passing into the fetus.

This theory is supported by the results of a separate analysis of the cadmium concentration in embryonal tissues from mice embryos, commissioned by the inventor. The results showed that the concentration of cadmium was very low, ranging from below about 4.4 nanomol/l to about 5.3 nanomol/l whereas the concentration of zinc in the same samples was in the range of 30-40 micromol/l. Further analytical work is ongoing.

Related studies commissioned by the inventor have shown that the exosomes in fetal calf serum are capable of absorbing zinc when zinc is added to said serum. Based on this, the present inventor postulates that the exosomes are similarly capable of absorbing cadmium. There is therefor a risk that donor blood and blood products may increase the cadmium load in a patient undergoing cancer treatment, and receiving blood transfusions or the administration blood products as part of the treatment, or for mitigating side effects of the treatment, such as anemia, compromised immune defense etc. In order to eliminate the risk that donor blood containing cadmium, or blood products containing cadmium are given to the patient, with possible negative consequences for example on metastasis, the inventor proposes a screening step of determining he cadmium content in donor blood, and discarding blood and blood products with a cadmium content exceeding the levels normally encountered in healthy subjects. Preferably the level of cadmium should be zero or as low as possible, and for some products this can be achieved by separating the exosome fraction and possibly replacing it with uncontaminated exosomes from a compatible source. The easiest approach to minimizing the concentration of cadmium in donor blood and products made thereof would be to request blood donors to indicate if they are smokers or not, and either disqualify them as donors, or mark the blood with an indication that it mustn't be administered to cancer patients.

In summary, the present inventor postulates that the capability of the placenta to prevent cadmium from passing into fetal tissues is of great significance for the rapid and practically error-free proliferation and differentiation of cells that takes place during gestation.

Conversely, when the mammalian organism is subjected to cadmium post partum and all through life, the disrupted balance between zinc and cadmium is likely to be a causative factor behind different disease, such as but not limited to cancer.

The findings of the present inventor form the basis for a new approach to the production of blood and serum products for use both in research, biotech production and in therapy.

LISTING OF EMBODIMENTS

1. A method in the manufacture of serum products, in particular fetal serum products, wherein the concentration of Zn(II) in the serum is determined and adjusted to a desired, specific value.
2. A method step in the manufacture of serum products, wherein the concentration of Zn(II) in the serum is determined and the concentration adjusted to a desired interval in the final product.
3. The method according to any one of embodiments 1 and 2, wherein the concentration of Zn(II) is adjusted to an interval of about 50 to about 200 µmol/l in the final product.
4. The method according to embodiment 1, wherein the concentration of Zn(II) is adjusted to about 50 µmol/l in the final product.
5. The method according to any one of embodiments 1 and 2, wherein the concentration of Zn(II) is adjusted to an interval of less than about 15 µmol/l, preferably less than about 10 µmol/l, more preferably less than about 5 µmol/l in the final product.
6. The method according to any one of embodiments 1 and 2, wherein the adjustment of the concentration of Zn(II) is performed by mixing fetal serum of at least two different serum batches having different concentrations of Zn(II) in a ratio such that the final concentration of Zn(II) is in an interval of about 50 to about 200 µmol/l in the final product.
7. The method according to any one of embodiments 1 and 2, wherein the adjustment of the concentration of Zn(II) is performed by subjecting fetal serum to ultracentrifugation and removing the formed pellet.
8. The method according to any one of embodiments 1 and 2, wherein the fetal serum is fetal serum from a mammal chosen from cattle, pig, horse, goat, cat, dog, and rabbit.
9. A method step in the manufacture or the preparation of fetal serum products, wherein the concentration of exosomes in the serum is determined, and the concentration in the final product is adjusted to a value within a desired interval.
10. A method step in the manufacture or the preparation of a fetal serum product based on fetal serum of a specific species, wherein the diameter of the exosomes is determined, and/or the concentration of Zn(II) in the exosomes in serum from said specific species is determined, whereupon the concentration of Zn(II) in the final product is adjusted a value within a desired interval.
11. A serum product, preferably a fetal serum product, manufactured according to the method of any one of embodiments 1-10.
12. A serum product, preferably a fetal serum product, having a concentration of Zn(II) adjusted to an interval of about 50-about 200 µmol/l.
13. A serum product, preferably a fetal serum product, having a concentration of Zn(II) adjusted to about 50 µmol/l.
14. A serum product, preferably a fetal serum product, having a concentration of Zn(II) adjusted to an interval of less than about 15 µmol/l, preferably less than about 10 µmol/l, more preferably less than about 5 µmol/l in the final product.
15. A serum product according to any one of embodiments 11 to 14, wherein the concentration of Zn(II) in said product is indicated on the package or in the accompanying product data sheet.
16. A method for in vitro cell or tissue culture using a culture medium containing a fetal serum product, wherein the concentration of Zn(II) in the culture medium is determined, and adjusted to a desired level.
17. The method according to embodiment 16, wherein the cells to be cultured are human cells, and the concentration of Zn(II) in the culture medium is adjusted to a value in the interval of 50-about 200 µmol/l.

18. The method according to embodiment 16, wherein the cells to be cultured are human cells, and the concentration of Zn(II) in the culture medium is adjusted to about 50 µmol/l.
19. The method according to embodiment 16, wherein the cells to be cultured are human cells, and the concentration of Zn(II) in the culture medium is adjusted to a value within an interval of less than about 15 µmol/l, preferably less than about 10 µmol/l, more preferably less than about 5 µmol/l in the final product/l.
20. A method for in vitro cell or tissue culture using a culture medium containing a fetal serum product, wherein the concentration of Zn(II) in the culture medium is determined, adjusted to a selected level, and maintained at said level during the duration of the culture and/or when repeating said culture.
21. An avian serum product, wherein manufactured according to the method of any one of claims 1-10 mutatis mutandis.
22. An avian serum product having a concentration of Zn(II) adjusted to an interval of about 50-about 200 µmol/l.
23. An avian serum product having a concentration of Zn(II) adjusted to about 50 µmol/l.
24. An avian serum product having a concentration of Zn(II) adjusted to an interval of less than about 15 µmol/l, preferably less than about 10 µmol/l, more preferably less than about 5 µmol/l in the final product.
25. An avian serum product according to any one of embodiments 11 to 14, wherein the concentration of Zn(II) in said product is indicated on the package or in the accompanying product data sheet.
26. A method for in vitro cell or tissue culture using a culture medium containing an avian serum product, wherein the concentration of Zn(II) in the culture medium is determined, and adjusted to a desired level.
27. The method according to embodiment 26, wherein the cells to be cultured are human cells, and the concentration of Zn(II) in the culture medium is adjusted to a value in the interval of 50-about 200 µmol/l.
28. The method according to embodiment 26, wherein the cells to be cultured are human cells, and the concentration of Zn(II) in the culture medium is adjusted to about 50 µmol/l.
29. The method according to embodiment 26, wherein the cells to be cultured are human cells, and the concentration of Zn(II) in the culture medium is adjusted to a value within an interval of less than about 15 µmol/l, preferably less than about 10 µmol/l, more preferably less than about 5 µmol/l in the final product/l.
30. A method for in vitro cell or tissue culture using a culture medium containing an avian serum product, wherein the concentration of Zn(II) in the culture medium is determined, adjusted to a selected level, and maintained at said level during the duration of the culture and/or when repeating said culture.
31. A method in the prevention, treatment, and/or alleviation of cancer in a mammal, wherein said mammal is subjected to a treatment reducing the amount of cadmium or changing the proportion of cadmium in relation to zinc in the body of said mammal.
32. The method according to the above embodiment, in combination with surgical removal of the tumor.
33. The method according to the above embodiment, in combination with surgical removal of the tumor and the administration of one or more cytostatic drug or drugs.
34. The method according to the above embodiment, in combination with radiation therapy.
35. The method according to the above embodiment, further involving the administration of a non-toxic dose of a metal chosen from iron, selenium and zinc, preferably zinc.
36. The method according to the above embodiment, wherein the reduction of the amount of cadmium or change of the proportion of cadmium in relation to zinc is performed by means of blood transfusion.
37. The method according to the above embodiment, wherein the reduction of the amount of cadmium or change of the proportion of cadmium in relation to zinc is performed by means of extracorporeal dialysis.
38. The method according to the above embodiment, wherein the reduction of the amount of cadmium or change of the proportion of cadmium in relation to zinc is performed by means of dietary adjustments.
39. A method step in the handling of donor blood, wherein the cadmium concentration in the blood is determined, and blood containing elevated concentrations of cadmium is disqualified for human use.
40. A method step in the collection of donor blood, wherein the donor is asked to indicate if he/she is a smoker or has been habitually smoking but stopped, in which case the donated blood is subjected to analysis for the cadmium content, and wherein blood containing elevated concentrations of cadmium is disqualified for human use.
41. A step in the treatment of cancer, wherein the cadmium level in the blood of the patient is determined, and an increased level compared to levels typical for a healthy population, is noted as a factor which potentially aggravates the disease and which motivates actions to lower the concentration of cadmium as a part of the treatment of cancer.

Without further elaboration, it is believed that a person skilled in the art can, using the present description, including the examples, utilize the present invention to its fullest extent. Also, although the invention has been described herein with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

Thus, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERENCES

Alkasalias, T et al., Inhibition of tumor cell proliferation and motility by fibroblasts is both contact and soluble factor dependent. Proc Natl Acad Sci USA. 2014 Dec. 2; 111 (48):17188-93

Darekar, S et al., Epstein-Barr virus immortalization of human B-cells leads to stabilization of hypoxia-induced factor 1 alpha, congruent with the Warburg effect, PLoS One. 2012; 7(7)

DeVita, V T Jr, Rosenberg S A. Two hundred years of cancer research, N Engl J Med. 2012 Jun. 7; 366(23):2207

Hanahan, D. and Weinberg R. A., The hallmarks of cancer, 2000, 100(1), 57-70

Hanahan, D. and Weinberg R. A., Hallmarks of cancer, the next generation, Cell. 2011 Mar. 4; 144(5):646-74

Klein, G, Evolutionary aspects of cancer resistance, in Semin Cancer Biol. 2014 April; 25:10-4

Luga, V et al., Exosomes mediate stromal mobilization of autocrine Wnt-PCP signaling in breast cancer cell migration, Cell. 2012 Dec. 21; 151(7):1542-56.

Meehan, K and Vella L J, The contribution of tumour-derived exosomes to the hallmarks of cancer, Crit Rev Clin Lab Sci. 2015 Oct. 19:1-11

Melo, S A et al., Glypican-1 identifies cancer exosomes and detects early pancreatic cancer, Nature. 2015 Jul. 9; 523(7559):177-82.

Valadi, H et al., Exosome-mediated transfer of mRNAs and microRNAs is a novel mechanism of genetic exchange between cells, Nat Cell Biol. 2007 June; 9(6):654-9.

What is claimed is:

1. A method in the prevention, treatment, and/or alleviation of cancer in a mammal, wherein said mammal is subjected to a treatment reducing the amount of cadmium or changing the proportion of cadmium in relation to zinc in the body of said mammal, wherein the reduction of the amount of cadmium or change of the proportion of cadmium in relation to zinc is performed by means of blood transfusion.

2. The method according to claim 1, in combination with surgical removal of a tumor.

3. The method according to claim 1, in combination with surgical removal of a tumor and administration of one or more cytostatic drug or drugs.

4. The method according to claim 1, in combination with radiation therapy.

5. The method according to claim 1, further involving the administration of a non-toxic dose of a metal chosen from iron, selenium and zinc.

6. The method according to claim 1, wherein the reduction of the amount of cadmium or change of the proportion of cadmium in relation to zinc is further performed by means of extracorporeal dialysis.

7. The method according to claim 1, wherein the reduction of the amount of cadmium or change of the proportion of cadmium in relation to zinc is further performed by means of dietary adjustments.

8. The method according to claim 1, further involving the administration of a non-toxic dose of zinc.

9. A method in the prevention, treatment, and/or alleviation of cancer in a mammal, wherein said mammal is subjected to a treatment reducing the amount of cadmium or changing the proportion of cadmium in relation to zinc in the body of said mammal, wherein the reduction of the amount of cadmium or change of the proportion of cadmium in relation to zinc is performed by means of extracorporeal dialysis.

10. The method according to claim 9, in combination with surgical removal of a tumor.

11. The method according to claim 9, in combination with surgical removal of a tumor and administration of one or more cytostatic drug or drugs.

12. The method according to claim 9, in combination with radiation therapy.

13. The method according to claim 9, further involving the administration of a non-toxic dose of a metal chosen from iron, selenium and zinc.

14. The method according to claim 9, wherein the reduction of the amount of cadmium or change of the proportion of cadmium in relation to zinc is further performed by means of dietary adjustments.

15. The method according to claim 9, further involving the administration of a non-toxic dose of zinc.

* * * * *